United States Patent [19]

Dressler

[11] Patent Number: 5,130,489
[45] Date of Patent: Jul. 14, 1992

[54] PROCESS FOR THE PREPARATION OF M-AMINOPHENOLS FROM RESORCINOL

[75] Inventor: Hans Dressler, Monroeville, Pa.

[73] Assignee: Indspec Chemical Corporation, Pittsburgh, Pa.

[21] Appl. No.: 498,980

[22] Filed: Mar. 26, 1990

Related U.S. Application Data

[63] Continuation-in-part of Ser. No. 266,326, Nov. 1, 1988, abandoned, which is a continuation-in-part of Ser. No. 878,685, Jun. 26, 1986, abandoned.

[51] Int. Cl.$^5$ .............. C07C 209/00; C07D 265/30; C07D 211/20; C07D 207/04
[52] U.S. Cl. ..................... 564/403; 544/173; 546/248; 548/570
[58] Field of Search ............... 564/403, 248; 548/570; 544/173

[56] References Cited

U.S. PATENT DOCUMENTS

| | | | |
|---|---|---|---|
| 2,376,112 | 5/1945 | Bean et al. | 260/574 |
| 3,102,913 | 9/1963 | Werner | 260/574 |
| 3,860,650 | 1/1975 | Becker et al. | 564/403 X |
| 4,380,669 | 4/1983 | Chang et al. | 564/402 |
| 4,400,537 | 8/1983 | Weil | 564/402 |
| 4,489,993 | 5/1984 | Slaugh | 564/402 |
| 4,609,760 | 9/1986 | Bohm et al. | 564/402 |

FOREIGN PATENT DOCUMENTS

| | | | |
|---|---|---|---|
| 149580 | 11/1979 | Japan | 564/403 WX |
| 1397098 | 8/1972 | United Kingdom | 564/403 |

*Primary Examiner*—Paul F. Shaver
*Attorney, Agent, or Firm*—Herbert J. Zeh, Jr.; Craig G. Cochenour

[57] ABSTRACT

An improved process is provided for producing m-aminophenols comprising reacting resorcinol and an amino compound in an inert organic solvent and in the presence of an aluminosilicate catalyst.

20 Claims, 1 Drawing Sheet

PROCESS FOR THE PREPARATION OF M-AMINOPHENOLS FROM RESORCINOL

CROSS REFERENCE TO RELATED APPLICATIONS

This application is a continuation-in-part of copending U.S. application Ser. No. 07/266,326 filed Nov. 1, 1988 which was a continuation of co-pending U.S. application Ser. No. 06/878,685 filed Jun. 26, 1986, now abandoned.

BACKGROUND OF THE INVENTION

1. Field of the Invention

The present invention relates to the preparation of m-aminophenols from resorcinol. More specifically, the present invention relates to the preparation of m-aminophenols by reacting anhydrous amine compounds selected from ammonia, primary amines or secondary amines with resorcinol in an organic solvent in the presence of certain silica alumina catalysts. In particular, the present invention relates to the preparation of the compound m-aminophenol by reacting anhydrous ammonia and resorcinol in an organic solvent in the presence of a natural or synthetic silica alumina catalyst.

2. Background of the Invention

The family of m-aminophenol compounds are well known and well reported in the literature. These compounds are useful as intermediates for preparing dyes, pharmaceuticals, resins and agrichemicals. More recently m-aminophenol compounds, particularly m-aminophenol itself, have found application in the preparation of high performance polymers, particularly in the preparation of intermediates for high performance fibers.

The most well known process for preparing aminophenols is by reacting resorcinol with an aminating agent selected from ammonia, primary amines and secondary amines. The compound m-aminophenol is most commonly prepared by reacting resorcinol with ammonia. The amination of resorcinol with aminating agents selected from ammonia, primary amines and secondary amines is well documented and is the subject of many patents and patent applications.

All of the methods comprise reacting resorcinol with the amine, however, there are many different variations of the reaction. For example, it is well known to react resorcinol with the amine in an aqueous medium. This is undesirable because of the necessity of stripping the water with a concomitant loss of product. In addition, the stability of m-aminophenol in aqueous mother liquors for recycle has been erratic. It has also been suggested to run the amination in various solvents with or without the use of various catalysts. Some of these methods have been somewhat successful, however, they suffer from one or more different drawbacks. For example, some catalysts are very expensive. Some catalysts cannot be recycled without being regenerated and some are difficult to separate from the reaction mixture. Some of the other deficiencies associated with the prior art processes include low conversion of resorcinol per pass, poor selectivity in the conversion to aminophenol with too high conversion to m-phenylenediamines, long reaction times and difficulty in isolating and/or purifying the m-aminophenol.

Accordingly, it is an object of this invention to provide an improved method for aminating resorcinol with ammonia, a primary amine or a secondary amine. It is a further object of this invention to provide a process for reacting resorcinol with ammonia, a primary amine or a secondary amine that combines high conversion of resorcinol to aminophenol compound with low amounts of m-phenylenediamine by-products and which does not suffer from the other drawbacks of the prior art processes for reacting resorcinol with amines.

SUMMARY OF THE INVENTION

Brief Description of the Invention

In accordance with the present invention, it has been found that m-aminophenols can be prepared from resorcinol and amines in high yield, with minimal formation of undesired by-products and with minimization of effluent for disposal. More particularly, the present invention comprises an improved process for reacting resorcinol with an aminating agent selected from ammonia, primary amines and secondary amines by running the reaction under anhydrous conditions in an inert organic solvent and in the presence of an aluminosilicate catalyst. The catalyst is a natural or synthetic zeolite or an activated clay which may be recycled.

DETAILED DESCRIPTION OF THE INVENTION

Figure 1:
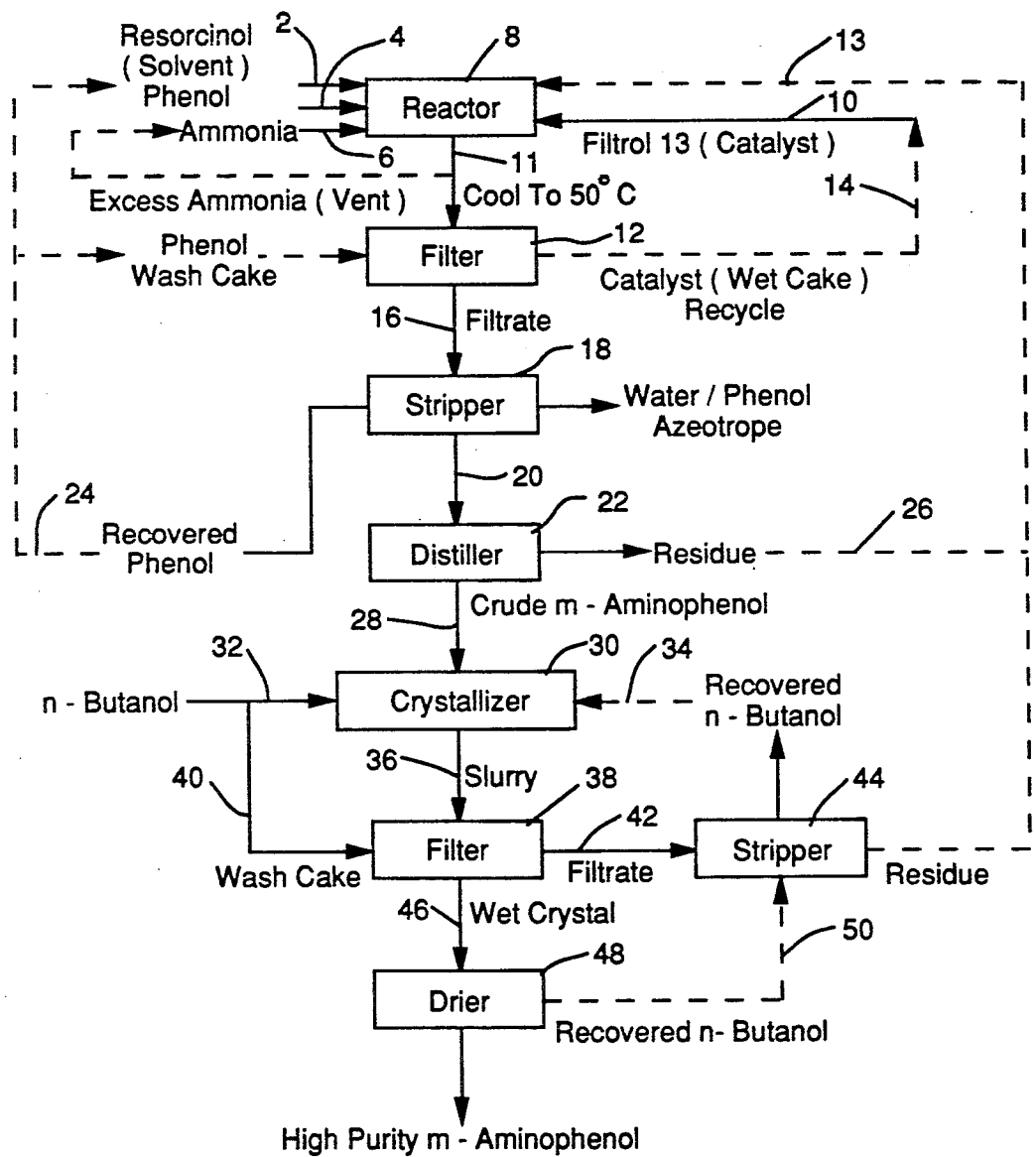
FIG. 1 is a flow diagram for preparing m-aminophenol from resorcinol and ammonia in accordance with the preferred embodiment of the present invention.

The present invention is directed to an improved process for preparing m-aminophenol compounds by reacting resorcinol with an aminating agent selected from ammonia, primary amines and secondary amines. The improvement comprises running the reaction with an anhydrous aminating agent in an organic solvent and in the presence of an aluminosilicate catalyst.

The aminating agents useful in the present invention are selected from ammonia, primary amines and secondary amines and are represented by the following general formula (a):

$$NHR_1R_2 \qquad (a)$$

where $R_1$ and $R_2$ are independently selected from H and alkyl groups of 1 to 12 carbon atoms. The alkyl groups may be primary, secondary, tertiary or cycloalkyl groups. $R_1$ and $R_2$ may together form a cyclic amine selected from piperidine, pyrrolidine, morpholine and alkyl derivatives thereof. The preferred aminating agent is selected from ammonia and primary or secondary amines having alkyl groups of 1 to 12 carbon atoms. The most preferred aminating agent is ammonia.

The aminating agents are reacted with resorcinol to form m-aminophenol or N-alkyl substituted m-aminophenol compounds represented by the following general formula (b):

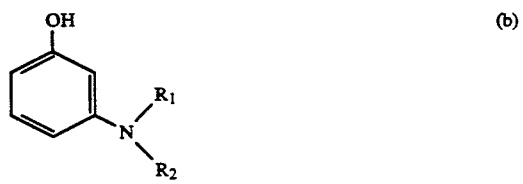

(b)

where $R_1$ and $R_2$ are as defined above.

In accordance with the present invention it is important that the aminating agent be anhydrous with the preferred aminating agent being anhydrous ammonia. If the reaction is run using an aqueous medium there is a resulting loss of product and a decrease in the stability of the product. Small amounts of water can be tolerated. Amounts of water exceeding 20 percent by weight based on the weight of resorcinol should be avoided.

In accordance with the present invention the reaction is performed in a suitable inert organic solvent. Examples of suitable solvents are hydrocarbons such as toluene, xylene and trimethylbenzene. Other suitable solvents are the phenols such as phenol itself, cresols, xylenols and alkyl phenols. It is important to note that the phenol solvents are not aminated under the conditions of the present process. One of the preferred solvents is phenol and the phenol is not aminated under the conditions of the present process, i.e., no aniline is detectable in the catalyzate.

In accordance with the present invention the reaction must be run in the presence of certain aluminosilicate catalysts. Examples of suitable catalysts are the zeolite (molecular sieve) catalysts which have a high silica/alimina ratio of from about 2 to about 100, which are preferably in the acid or ammonium-exchanged form such as Union Carbide's LZ M-8 (mordenite structure) and LZ Y-62 (Y-type molecular sieve). Other suitable catalysts include Union Carbide's SK-500 (a rare earth exchanged zeolite), and activated clays (aluminosilicates) such as United Catalyst's montmorillonite K-306 and Filtrol/Harshaw's Filtrol 13 or Filtrol 24 (beidellite activated clay). The amount of catalyst employed will depend on the particular catalyst but generally from about 10 to about 100% parts by weight of the resorcinol is employed.

The resorcinol and aminating agent are reacted in molar ratios of resorcinol to aminating agent of from 1:1 to 1:5 and preferably from 1:1.5 to 1:3.0. Ratios outside of these ranges may be employed but are not desirable. For example, ratios of less than 1:1 decrease the yield of desired product without any increase in reactivity or selectivity. In addition, ratios of greater than 1:5 do not increase the yield, reactivity or selectivity. Such excess aminating agent also creates a handling problem.

The resorcinol and aminating agent are reacted at temperatures of between 175° C. and 275° C., preferably between 200° C. and 240° C. If the temperature is too low, the reaction rate is low and the conversion is low. If the temperature is too high, the formation of undesirable by-products increases, i.e., the selectivity to m-aminophenol decreases. The reaction is run at autogenous pressures.

When the reaction is complete as evidenced by such methods as spectroscopic or chromatographic analysis, the crude m-aminophenol solution is isolated by filtration. The catalyst is then washed, the solvent stripped from the combined filtrate and wash, and the crude m-aminophenol is flash distilled and recrystallized from a suitable medium such as methanol, ethanol (95 or 100%), butanol or solvent mixtures such as toluene/butanol, to give white m-aminophenol of high purity and stability.

In accordance with the present invention it has been found that the catalyst can be recycled many times before it needs regenerating. It has also been found that the unreacted aminating agent and solvent can readily be recycled without any deleterious effect on the product or process. Thus, the overall process is economical and environmental problems are minimized.

In FIG. 1, there is illustrated a flow diagram of a preferred process for making m-aminophenol in accordance with the present invention. Referring now to FIG. 1, resorcinol through conduit 2, phenol via conduit 4 and anhydrous ammonia via conduit 6 are fed to reactor 8 where they are contacted with catalyst (Filtrol-13-LM) from conduit 10 and a recycle stream comprising resorcinol, m-aminophenol and m-phenylenediamine via conduit 13. The reaction is conducted at 220° C. ±5° C. at 180-220 psig for 5 hours. After reaction is complete, the reaction mixture is cooled to 50°-150° C. and the residual pressure is released. Excess ammonia can be vented at a higher temperature such as 150° C. and recycled via conduit 6. The charge is then passed via conduit 11 to filter 12 and filtered at 50°-150° C. The catalyst (wet cake) is washed with molten phenol and recycled via conduit 14 to reactor 8. The combined filtrate and wash are passed via conduit 16 to atmospheric stripping unit 18 where the water formed in the reaction is removed as a water/phenol azeotrope at about 100° C., then the remainder is stripped under vacuum to 150° C. (pot) at 20 torr to remove the phenol, b.p. −86° C./20 torr. The phenol is recycled both to filter 12 and reactor 8 via conduit 24. From the phenol stripping unit, the residual crude m-aminophenol is passed via conduit 20 to vacuum distillation unit 22 where a m-aminophenol fraction is recovered at 160°-163° C. (head) and 10 torr. The residue is recycled to reactor 8 via conduit 26. The crude reaction product contains resorcinol, m-aminophenol and m-phenylenediamine and is passed from distillation unit 22 via conduit 28 to crystallizer 30 where it is treated with an equal amount of hot n-butanol from conduits 32 and 34. After cooling to 25° C., the slurry is passed via conduit 36 to filter 38 and the resultant white solids passed via conduit 46 to vacuum drier 48 operated at ca. 100° C., 20 torr where 97-98% pure m-aminophenol is recovered (m.p. 120°-121° C.). The combined filtrate and wash from filter 38 are passed via conduit 42 to solvent stripper 44, the recovered n-butanol passed via conduit 34 to crystallizer 30 and also used to wash the filter cake at filter 38, and the residue comprising resorcinol, m-aminophenol and m-phenylenediamine recycled to reactor 8 via conduit 13. The wet crystals from filter 38 are passed via conduit 46 to drier 48 and vacuum dried to produce high purity m-aminophenol and the n-butanol recovered from the drier is recycled via conduit 50 to solvent stripper 44.

The following examples serve to further illustrate the invention and the preferred embodiments thereof. All parts and percentages in the examples and elsewhere in the specification and claims are by weight unless otherwise indicated.

EXAMPLE 1

A 1-gal. autoclave was charged with 440.0 g (4.0 m) resorcinol, 1600 ml. of xylene, 220.0 g of Union Carbide catalyst LZM-8 powder (a synthetic zeolite with mordenite structure, ammonium ion exchanged) and 204.0 g (12.0 m) of anhydrous ammonia. The autoclave was sealed, stirred, heated to 220° C. and held at 217°-220° C. for 5 hrs. The reactor was then cooled to 25° C., vented, discharged, and the product filtered. The catalyst cake was washed with methanol and the combined filtrate and wash was stripped to final conditions of 110° C. (pot)/20 torr. The dark-colored residue, by LC analysis, contained 82 wt. % m-aminophenol, 5.7 wt. % resorcinol, and 9.0 wt. % m-phenylenediamine.

EXAMPLES 2-5

Example 1 was repeated in identical manner, except that the used, dried catalyst from the preceding run was used again in the succeeding runs. The average composition of the product over examples 1-5 was 80.6 wt. % m-aminophenol, 9.0 wt. % resorcinol, and 8.4 wt. % m-phenylenediamine. The average recovery of the crude product over five runs was 96.5 wt. %. Resorcinol conversion averaged 91% per pass; the calculated ultimate yield of m-aminophenol was 88.6%.

The crude product was flash-distilled at 10 torr to give 95.6 wt. % distillate (light yellow color) and 3.3 wt. % residue. The flash-distilled product was recrystallized from methanol to give a white, crystalline product, estimated to be 99.3% pure by DSC (differential scanning calorimetry) and 98.8% pure m-aminophenol by LC analysis, m.p. 123.0°-123.5° C.

EXAMPLES 6-14

A series of examples were run using the general procedure set forth in Example 1 but with different ratios of ingredients, solvents, catalysts and reaction conditions. The results for this series are set forth in Table 1.

TABLE 1

Amination of Resorcinol with Ammonia

| Ex. No. | m. R./m. NH$_3$ | Solvent | Catalyst, Wt. %[a] | Temp., °C. | Time, hrs. | Product, Wt. %[d] MAP | R | MPDA |
|---|---|---|---|---|---|---|---|---|
| 6 | 1.0/3.0 | Toluene | LZM-8, 100 | 220-234 | 1.5 | 78 | 8.3 | 5.1 |
| 7 | 1.0/2.0 | Toluene | LZM-8, 25 | 236-242 | 5 | 76 | 11.5 | 7.6 |
| 8 | 1.0/3.0 | Xylene | Mont. K-306, 50 | 237-240 | 4 | 75 | 13 | 6.0 |
| 9 | 1.0/3.0 | Xylene | Mont. K-306, (used)[b] | 237-240 | 4 | 73 | 17.5 | 4.9 |
| 10 | 1.0/3.0 | Xylene | Mont. K-306, (used)[c] | 238-241 | 5 | 79 | 16 | 5.5 |
| 11 | 1.0/2.0 | Phenol | Mont. K-306, 50 | 219-231 | 4 | 71 | 18 | 8.0 |
| 12 | 1.0/2.0 | Xylene | SK-500, 50 | 217-240 | 1.0 | 71 | 17 | 4.0 |
| 13 | 1.0/3.0 | Toluene | LZY-62, 50 | 218-223 | 5 | 65.5 | 22 | 6.2 |
| 14 | 1.0/3.0 | 1,2,4-Trimethylbenzene | Fil. 13-LM, 50 | 226-233 | 5 | 72.5 | 12 | 4.0 |

[a]Catalyst LZM-8 - Union Carbide, synthetic mordenite; Mont. K-306 = United Catalysts, Montmorillonite Clay; SK-500 = Union Carbide, rare earth exchanged synthetic zeolite; LZY-62 = ammonium exchanged Y-type molecular sieve; Fil, 13-LM = Filtrol Corp., acid clay. The wt. % is based on the resorcinol charged.
[b]Used catalyst from run 8.
[c]Used catalyst from run 9.
[d]MAP = m-aminophenol, R = resorcinol, MPDA = m-aminophenylenediamine.

EXAMPLE 15

A 2-liter autoclave was charged with 220.0 g (2.0 m.) of resorcinol, 880.0 g of phenol (solvent), 292.4 g (4.0 m.) diethylamine and 88.0 g of Filtrol-13LM (catalyst). The autoclave was sealed, stirred and held at 215√-220° C. for 5 hrs. The charge was then cooled to ca. 60° C. The autoclave was vented and the catalyst was filtered. The catalyst cake was washed with warm (60° C.) phenol. The combined filtrate and wash were stripped of unreacted diethylamine; water formed in the reaction and solvent (phenol) were removed by distillation. The residue was flash-distilled at 10 torr to give a product containing, by LC (liquid chromatographic) analysis, 38.5 wt. % resorcinol and 62.8 wt. % m-diethylaminophenol.

EXAMPLE 16

In accordance with the general procedure of Example 1, m-pyrrolidinylphenol can be prepared by charging a 2-liter autoclave with 220.0 g (2.0 m) of resorcinol, 880.0 g of phenol (solvent), 284.5 g (4.0 m) of pyrrolidine and 88.0 g of Filtrol 13LM (catalyst). The autoclave will then be sealed, stirred and held at 215°-220° C. for 4 hrs. The product would then be filtered, the filtrate stripped of low boilers and flash distilled to provide a product containing m-pyrrolidinylphenol which can be identified by IR/NMR analysis.

EXAMPLE 17

In accordance with the general procedure of Example 1, a 2-liter autoclave was charged with 330.0 g (3.0 m) resorcinol, 268.5 g (3.6 m) diethylamine, 330.0 g of phenol, and 132.0 g of Filtrol - 13LM. The charge was reacted for 5 hrs. at 220° C. and then filtered, the filtrate stripped of low boilers and flash distilled to provide a product containing 61 wt. % m-diethylaminophenol and 33 wt. % resorcinol by LC analysis. Based on the resorcinol converted, a 91 wt. % yield of m-diethylaminophenol was obtained.

EXAMPLE 18

In accordance with the general procedure of Example 1, m-propylaminophenol can be prepared by charging a 2-liter autoclave with 220.0 g (2.0 m) of resorcinol, 880.0 g of phenol (solvent), 236.4 g (4.0 m) of propylamine and 110.0 g of Filtrol 13-LM (catalyst). The autoclave will be sealed, stirred and held at 220° C. for 5 hours. The charge will be then cooled, vented, discharged and filtered. The filtrate will be stripped of low boilers, including the phenol solvent, and the crude product vacuum-distilled. This distillate will contain a substantial amount of m-propylaminophenol (by IR/NMR analysis).

EXAMPLE 19

In accordance with the general procedure of Example 1, m-cyclohexylaminophenol can be prepared by charging a 2-liter autoclave with 220.0 g (2.0 m) of resorcinol, 880.0 of phenol (solvent), 297.6 g (3.0 m) of cyclohexylamine, and 88.0 g of Filtrol 13-LM (catalyst). The autoclave will be sealed, stirred and held at 220° C. for 5 hours. The reactor will be cooled, vented and discharged. The catalyzate will be filtered and the filtrate stripped of low boilers, including the phenol solvent. The residual, crude product can be analyzed by IR/NMR methods and will be found to contain a substantial amount of m-cyclohexylaminophenol.

EXAMPLE 20

In accordance with the general procedure of Example 1, m-amylaminoresorcinol can be prepared by charging a 2-liter autoclave with 220.0 g (2.0 m) of resorcinol, 880.0 of phenol (solvent), 348.7 g (4.0 m) of amylamine, and 88.0 g of Filtrol 13-LM (catalyst). The autoclave will be sealed, stirred and held at 220° C for 5 hours. The reactor will then be cooled, vented and discharged. The catalyzate will be filtered and the filtrate stripped of low boilers, including the phenol solvent. The residue will be anaylzed by IR/NMR techniques and found to contain a considerable amount of m-amylaminoresorcinol, with a good conversion of the resorcinol charged.

While the above is illustrative of preferred embodiments and the best mode, numerous variations may occur to one of ordinary skill and thus the invention is intended to be limited only by the appended claims.

What is claimed is:

1. An improved process for preparing m-aminophenols of the formula

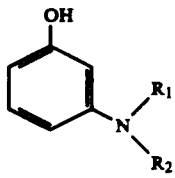

where $R_1$ and $R_2$ are independently selected from H and alkyl groups of from 1 to 12 carbon atoms or where $R_1$ and $R_2$ together form a cyclic amine selected from piperidines, pyrrolidines and morpholines, comprising reacting resorcinol with an anhydrous aminating agent selected from ammonia, primary amines and secondary amines represented by the formula

HNR$_1$R$_2$ where $R_1$ and $R_2$ are as defined above; wherein the improvement comprises running the reaction in an inert organic solvent with said anhydrous aminating agent in the presence of a silica alumina catalyst.

2. A process as in claim 1 wherein the catalyst has a silica to alumina ratio of from 2 to about 100.

3. A process as in claim 1 wherein the catalyst is an activated clay.

4. A process as in claim 1 wherein the organic solvent is selected from toluene, xylene, trimethyl benzene, phenol, cresol, xylenol and alkyl phenols.

5. A process as in claim 1 wherein the ratio of resorcinol to aminating agent is from 1:1 to 1:5.

6. A process as in claim 2 wherein the ratio of resorcinol to aminating agent is from 1:1 to 1:5.

7. A process as in claim 4 wherein the ratio of resorcinol to aminating agent is from 1:1 to 1:5.

8. A process as in claim 7 wherein the catalyst has a silica to alumina ratio of from 2 to about 100.

9. A process as in claim 7 wherein the catalyst is an activated clay.

10. A process as in claim 1 wherein the catalyst is employed in an amount of about 10 to 100 percent by weight based on resorcinol.

11. An improved process for preparing m-aminophenol by reacting resorcinol with ammonia, wherein the improvement comprises running the reaction in an inert organic solvent with anhydrous ammonia in the presence of a silica alumina catalyst.

12. A process as in claim 11 wherein the catalyst has a silica to alumina ratio of from 2 to about 100.

13. A process as in claim 11 wherein the catalyst is an activated clay.

14. A process as in claim 11 wherein the catalyst is employed in an amount of about 10 to 100 percent by weight based on resorcinol.

15. A process as in claim 12 wherein the catalyst is employed in an amount of about 10 to 100 percent by weight based on resorcinol.

16. A process as in claim 13 wherein the catalyst is employed in an amount of about 10 to 100 percent by weight based on resorcinol.

17. A process as in claim 11 wherein the ratio of resorcinol to ammonia is from 1:1 to 1:5.

18. A process as in claim 14 wherein the ratio of resorcinol to ammonia is from 1:1 to 1:5.

19. A process as in claim 15 wherein the ratio of resorcinol to ammonia is from 1:1 to 1:5.

20. A process as in claim 16 wherein the ratio of resorcinol to ammonia is from 1:1 to 1:5.

* * * * *